United States Patent [19]

Stewart

[11] 4,347,205
[45] Aug. 31, 1982

[54] PROCESS FOR PREPARING AN INFLATABLE PAD FOR A FACE MASK

[75] Inventor: Mervin Stewart, Waringstown, Ireland

[73] Assignee: Warne Surgical Products Limited, Andover, England

[21] Appl. No.: 131,743

[22] Filed: Mar. 19, 1980

[30] Foreign Application Priority Data

Apr. 3, 1979 [GB] United Kingdom ............... 7911512

[51] Int. Cl.³ ............................................. B29H 3/042
[52] U.S. Cl. ................................... 264/130; 264/264; 264/279.1; 264/307; 427/430.1
[58] Field of Search ............... 427/430.1; 264/264, 264/267, 279, 130, 279.1, 307

[56] References Cited

U.S. PATENT DOCUMENTS 2,373,529  4/1945  Beal ................................. 264/264 X
4,263,237  4/1981  Weeden et al. ................ 264/267 X

FOREIGN PATENT DOCUMENTS 841104   7/1960  United Kingdom .
842642   7/1960  United Kingdom .
1101099  1/1965  United Kingdom .
1272576  5/1972  United Kingdom .

Primary Examiner—Evan K. Lawrence
Attorney, Agent, or Firm—Lane, Aitken, Kice & Kananen

[57] ABSTRACT

A method of preparing an inflatable pad for a face mask in which a former (3) is coated with a curable composition which is cured to provide an elastic air-impermeable sheath (4) of rubber or like polymer which does not adhere to the former, thereby defining an inflation chamber. The former comprises a sheet of flexible material, e.g. polymer foam and remains within the pad in use thereby avoiding the conventional operations of slitting the air-impermeable sheath, removing the former and resealing the air-impermeable sheath.

9 Claims, 1 Drawing Figure

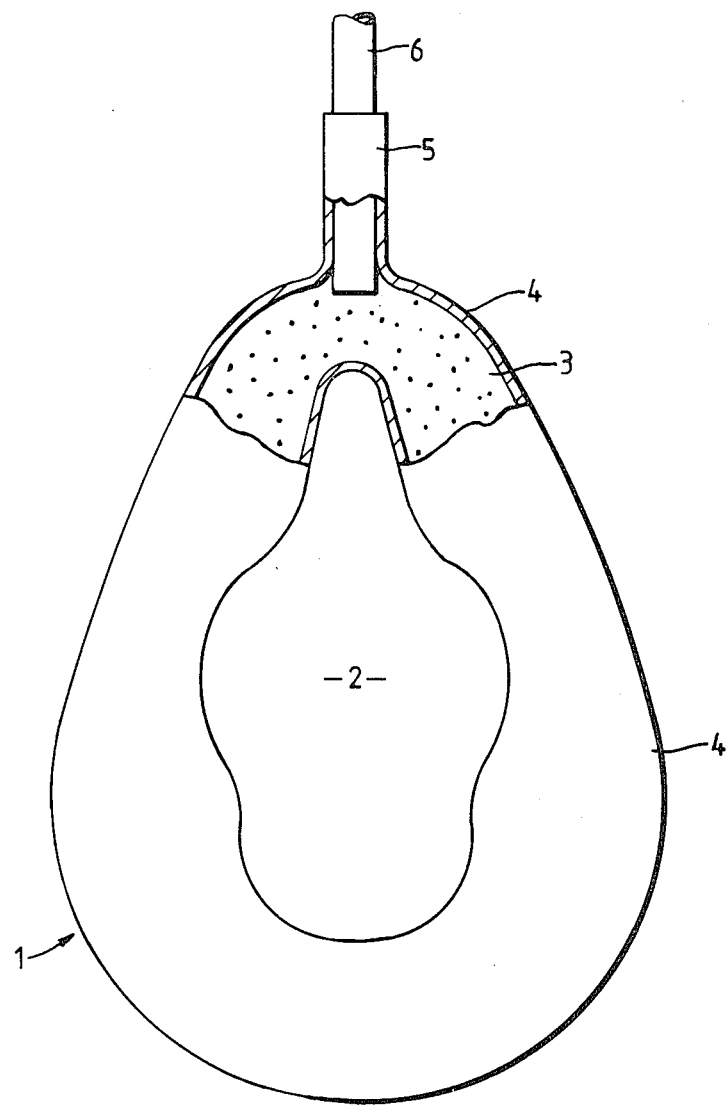

PROCESS FOR PREPARING AN INFLATABLE PAD FOR A FACE MASK

This invention relates to face masks of the type designed to be fitted over the mouth and nose of a person for the supply of oxygen or other gas. In particular the invention relates to the production of an inflatable pad for such a face mask which pad provides a comfortable seal between the face and the mask.

Inflatable pads for face masks are known. These pads comprise an inflatable rubber ring which is substantially ovoid and shaped to conform with the contours of the face. The inflated pad is contacted with the face under gentle pressure and provides a soft cushion forming a gastight seal with the face.

The pads are generally made by coating, normally by dipping, a former, which is shaped to correspond with the desired configuration of the inflated pad, with a rubber latex which is then dried to provide a rubber sheath. After drying, the former is removed by cutting a slit in the rubber sheath and thereafter the slit is sealed. A tube for supplying air to the interior of the pad is either formed during the coating operation or applied to the pad after curing. The mask is completed by attaching a cone to the pad, and over dipping the entire assembly with latex and the curing.

The former used for preparing the pad is usually made of rubber and is shaped to correspond with the configuration of the inflated pad. The former is generally elliptical in cross-section and is cut through in one place so that the ring may be opened to facilitate removal from the rubber sheath. The operations of stripping the pad from the former and sealing the slit through which the former is removed are time consuming and labour intensive.

It is an object of the present invention to provide a method for the production of inflatable pads for face masks in which the above problems are obviated.

Therefore according to the invention there is provided a process for preparing an inflatable pad for a face mask of the type described in which a suitably contoured flat section former which is shaped to correspond with the desired configuration of the inflatable pad is completely coated with a curable composition and the coating cured to provide an elastic air-impermeable sheath which is releasable from said former defining an annular inflation chamber, the coating being conducted in such a manner as to provide a conduit for entry of gas into the inflation chamber, the former remaining within the inflation chamber and comprising a flexible material such that it will conform to and remain within the inflated pad.

The inflatable pad comprises an annulus of elastic air-impermeable material defining an inflation chamber which may be inflated by air, the inflatable pad containing within the inflation chamber a former upon which the elastic air-impermeable material is coated, the former comprising a flexible material such that when the pad is inflated it will remain within the inflated pad.

The process of the invention has the advantage that the former used in the production is not removed from the inflation chamber and the pad is used with the former in place. In order for the pad to be effective, the former must be made of a flexible material so that when the pad is inflated and used the former deforms and remains within the pad without any rigid protruberances which would be uncomfortable and destroy the seal between the face and mask. The former is preferably made of a soft material such as a rubber or polymer foam, e.g. polyurethane foam, although any other suitable material, e.g. a fabric, may be used.

The former is preferably substantially planar, the resulting pad being essentially two dimensional before inflation. The former is shaped so that the inflated pad has the required configuration to cover the nose and mouth and conform with the contours of the face for efficient sealing. In the case of a planar former, the outer shape is substantially ovoid. The centre portion of such a former which is removed to provide the aperture for the nose and mouth may be substantially ovoid or pear-shaped as in the conventional pads. However, it has been found that the pad has a smoother contact surface with the face if extra areas or bulges are cut out on either side of the ovoid at about half the distance along the major axis of the ovoid.

The use of a substantially planar former also has the advantage that the formers may be readily stamped out from a sheet of material and thus the moulding and shaping operations which are required to produce the 3-dimensional conventional formers are dispensed with.

The curable compositions with which the formers are coated may be any composition which upon curling or cross-linking will provide an elastic air-impermeable sheath or skin. Suitable materials include synthetic or natural rubber latices or compositions forming polyurethanes, polyesters, silicones, etc. The compositions may conveniently be applied by dipping the former in a solution or suspension of the compounds. Other methods of application include spraying and brushing. The components of the curable composition may be applied in a single operation or in two or more stages. The cross-linked coating or sheath must not adhere to the former and therefore the former may be treated with a release coating if required.

After curing or cross-linking the pad is inflated and the complete mask assembled in the normal manner.

The invention will now be described with reference to the FIGURE which represents an inflatable pad (uninflated) in accordance with the invention with part of the cured sheath removed.

The pad 1 is ovoid in shape having a central aperture 2 shaped so that the mask fits snugly over the nose and mouth. The pad is substantially planar having been formed by coating a flat former 3 of polyurethane foam. The pad has an outer sheath 4 formed of a medical grade rubber. A conduit or tail 5 for the entry of gas into an inflation chamber between the former 3 and the sheath 4 is formed during the coating operation by coating a cylindrical rod 6 which was used to support the former. The rod 6 may readily be removed and the pad inflated and the complete mask assembled. The thickness of the former 3 may vary, although a thickness of 2 to 4 mm of a polyurethane foam sheet provides satisfactory characteristics. The thickness of the rubber must be sufficient to withstand the inflation pressure in use, e.g. 1 to 2 mm.

The invention will now be illustrated by the following Example.

EXAMPLE

Face masks having an inflatable pad as illustrated in the FIGURE were prepared as follows:
(1) Formers having an ovoid shape including a pointed end and an opposite base end were cut from a sheet 2 mm thick of polyethylene foam with a guillotine.

(2) The formers were placed in a dipping frame supported from their pointed ends by a cylindrical support as shown in the accompanying drawing. Each frame may hold a number of formers, e.g. 20.

(3) The formers were dipped in a release coagulant solution comprising calcium nitrate and calcium carbonate in industrial methylated spirits. The formers were withdrawn slowly and inverted (i.e. formers having the base end upwards).

(4) The treated formers (still inverted) were dried, e.g. in a drying oven for 10 minutes.

(5) The formers were dipped in a tank containing medical grade rubber latex controlling the immersion to maintain a slow steady movement until completely submerged. After a dwell time of 2 minutes the resulting pads were withdrawn at a slow steady speed.

(6) The bottom of the pads were dipped to a depth of about 1 inch in a coagulant solution. The coagulant step is to prevent latex running off the bottom of the former or forming drips which would harden upon curing to form hard pimples which are both unsightly and uncomfortable when the pad is used.

(7) The pads were dried and cured, e.g. in an oven for 15 minutes at 60° C.

(8) The finished pads were removed from the frame, inflated and the tail tied, placed on a template and the completed mask assembled in a conventional manner. The cone of the mask was adhered to the pad by applying adhesive to an edge of the cone only.

I claim:

1. A process for preparing an inflatable pad for a face mask comprising providing a substantially planar former which is shaped to correspond with the desired configuration of the pad, coating all surfaces of said former with a curable composition which when cured is elastic, air-impermeable and releasable from said former, curing said coating to provide an elastic air-impermeable sheath completely covering said former which is releasable from said former to define an inflation chamber, the coating being conducted in such a manner as to provide a conduit in said sheath for entry of gas into said inflation chamber to inflate said sheath, the former remaining within the inflation chamber and comprising a flexible material which will remain within and conform to the contours of the inflation chamber when the chamber is inflated.

2. A process according to claim 1 wherein said former is cut from a sheet of polymer foam material.

3. A process according to claim 2 wherein the foam material comprises polyurethane or polyethylene foam.

4. A process according to claim 3 wherein the former has a thickness of from 2 to 4 mm.

5. A process according to claim 1 wherein the former is provided with a release coating to prevent adherence of the air-impermeable sheath.

6. A process according to claim 1 wherein the curable coating is applied by dipping the former into a solution or suspension of the curable composition.

7. A process according to claim 1 wherein the curable composition comprises a synthetic or natural rubber latex or a composition forming a polyurethane, polyester or silicone elastomeric material upon curing.

8. A process according to claim 1 wherein the former is held on a cylindrical support during the coating operation, which support also serves as a former for moulding the conduit for entry of gas into the inflation chamber, said support being readily removable from said sheath.

9. A process for preparing an inflatable pad for a face mask comprising the steps of:
(1) preparing a former from a flexible sheet of polymer foam having a thickness of 2 to 4 mm, said former having a substantially ovoid shape and being shaped to correspond to the desired configuration of the pad,
(2) placing the former on the end of a cylindrical support, said support being readily removable from a curable composition to be applied, so that the former is supported from its pointed end,
(3) dipping the former in a release coagulant solution to prevent adherence of a curable composition to be applied and withdrawing said former,
(4) drying the coated former,
(5) dipping said former in a solution or suspension of said curable composition which when cured is elastic, air impermeable and releasable from the former, so that all surfaces of the former and the portion of the support adjacent said former are coated, and steadily withdrawing the former,
(6) dipping the bottom of the former into a coagulant solution to prevent curable composition running off the bottom of the former;
(7) curing the coated former at elevated temperature to form an inflation chamber between the former and the cured composition, and
(8) removing said cylindrical support to form a conduit for entry of gas into the inflation chamber.

* * * * *